United States Patent [19]

Rosenthale et al.

[11] Patent Number: 4,707,495
[45] Date of Patent: Nov. 17, 1987

[54] PEPTIC ULCER TREATMENT METHOD

[75] Inventors: Marvin E. Rosenthale, Princeton; David A. Shriver, Martinsville; Laurence B. Katz, Lawrenceville, all of N.J.

[73] Assignee: Ortho Pharmaceutical, Raritan, N.J.

[21] Appl. No.: 791,673

[22] Filed: Oct. 28, 1985

[51] Int. Cl.$^4$ ........................................... A61K 31/215
[52] U.S. Cl. ................................... 514/530; 514/927; 514/573; 514/690; 514/678
[58] Field of Search ............... 514/530, 573, 678, 690, 514/927

[56] References Cited

U.S. PATENT DOCUMENTS

| 4,097,603 | 6/1978 | Robert | 514/530 |
|---|---|---|---|
| 4,198,521 | 4/1980 | Floyd et al. | 560/118 |
| 4,210,669 | 7/1980 | Shimomura | 514/530 |
| 4,254,145 | 3/1981 | Birnbaum | 424/305 |

OTHER PUBLICATIONS

Birnbaum J. E., Chan P. S., Cervoni P.: Cutaneous Erythema and Blood Pressure Lowering Effects of Topically Applied 16-Vinylprostaglandins, Prostaglandins 23: 185–199, 1982.
Cervoni P., Chan P. S., Lie F. M., Birnbaum J. E.: CL 115,347 (DHV-PGE$_2$ME): A New Orally and Topically Active Prostaglandin Antihypertensive Agent, Federation Proc. 42:157–161, 1983.
Hunt J. N., Smith J. L., Jiang C. L., Kessler L.: Effect of a Synthetic Prostaglandin E$_1$ Analog on Aspirin-Induced Gastric Bleeding and Secretion, Dig Dis Sci 28: 897–902, 1983.
Reele S. B., Bohan D.: Oral Antisecretory Activity of Prostaglandin E$_2$ in Man, Dig Dis Sci 29: 390–393, 1984.
Robert A.: Prostaglandins: Their Effect on the Digestive System, Viewpoints on Digestive Disease 2:1–4, 1979.
Robert A., Nezamis H. E., Lancaster C., Hanchar A. J.: Cytoprotection by Prostaglandins in Rats, Prevention of Gastric Necrosis Produced by Alcohol, HCl, NaOH, Hypertonic NaCl, and thermal Injury, Gastroenterology 77: 433–443, 1979.
Shay H., Sun D. C., Gruenstein M.: A Quantitative Method for Measuring Spontaneous Gastric Secretion in Rat, Gastroenterology 26: 906–913, 1954.
Johansson C., Bergstrom S.: Prostaglandins and Protection of the Gastroduodenal Mucosa, Scand J Gastroenterol, Suppl. nr 77, 17: 21–46, 1982.

Primary Examiner—Frederick E. Waddell
Attorney, Agent, or Firm—Benjamin F. Lambert

[57] ABSTRACT

A method of treating peptic ulcer disease by topical application of a prostaglandin analog is described.

7 Claims, No Drawings

PEPTIC ULCER TREATMENT METHOD

DESCRIPTION

TECHNICAL FIELD

The present invention relates generally to a method of treatment for peptic ulcers and particularly to an ulcer treatment method that utilizes a synthetic prostaglandin analog that is applied topically to the skin of a mammal to be treated.

BACKGROUND ART

Prostaglandins are a family of 20 carbon, oxygen-containing fatty acids that are biochemically derived from arachidonic acid. There are approximately twenty naturally occurring prostaglandins and numerous analogs or congeners have been synthesized.

The reduction of the acid burden of the gastrointestinal tract has long been recognized as a potential therapeutic approach for the management of peptic ulcer disease. Prostaglandin $E_1$ ($PGE_1$), prostaglandin $E_2$ ($PGE_2$) and several PGE analogs or congeners have been shown to have gastric antisecretory activity in both laboratory animals and man. However, the clinical usefulness of these compounds as gastric antisecretory agents has been limited by the appearance of gastrointestinal side effects, namely nausea, vomiting, intestinal colic and diarrhea.

There is, however, another action of some prostaglandins on the gastrointestinal tract that appears to be unrelated to their ability to inhibit gastric acid secretion. This action is called "cytoprotection".

The word cytoprotection is used to describe the ability of some prostaglandins to increase the natural integrity of the gastrointestinal mucosa. The cytoprotective activity of a compound can be observed in both animals and man by noting the increased resistance of the gastrointestinal mucosa to the noxious effect of strong irritants, e.g., the ulcerogenic effects of aspirin or indomethacin. In addition to lessening the effect of nonsteroidal anti-inflammatory drugs on the gastrointestinal tract, animal studies show that cytoprotective prostaglandins prevent gastric lesions induced by oral administration of strong acids, strong bases, ethanol, hypertonic saline solutions, and even boiling water. Prostaglandins and prostaglandin analogs that exhibit a cytoprotective effect in laboratory animals have been shown to provide cytoprotection in humans. See Johansson and Bergstrom, *Scand. J. Gastroenterol.* suppl. Nr. 77, 17, 21–46 (1982), and the citations therein.

The cytoprotective activity of prostaglandins does not appear to be related to their ability to inhibit gastric acid secretion because:

(a) The cytoprotective unit dose is typically a small fraction of the antisecretory dose in the case of prostaglandins that exhibit gastric acid antisecretory activity. In many cases, the antisecretory $ED_{50}$ is more than 100 times higher than the cytoprotective dose.

(b) Certain cytoprotective prostaglandins, e.g., 16,16-dimethyl $PGA_2$, and 15(R)-15 methyl $PGF_{2\beta}$, are not antisecretory at any dose when given orally to rats.

(c) Other antisecretory agents such as cimetidine and methscopolamine bromide, as well as antacids, are not cytoprotective in the models employed. Robert et al., *Gastroenterology*, 77: 433–443, (1979).

In addition, cytoprotective activity does not appear to be a property of all prostaglandins since oral administration of either $PGA_1$ or $PGD_2$ does not protect rats from indomethacin-induced gastric lesions. *Advances in Prostaglandin and Thromboxane Research*, Vol. 2, Samuelsson and Paoletti eds., Raven Press, New York, N.Y., pages 507–520, (1976).

There is no apparent general structure-activity relationship for compounds exhibiting cytoprotective activity. Cytoprotective prostaglandins have no broadly common structural configuration, therefore, it is not possible to predict which prostaglandins or prostaglandin analogs will exhibit cytoprotective activity and which will not.

Treatments to obtain a cytoprotective or antisecretory effect with prostaglandins or prostaglandin analogs have heretofore been generally by oral, enteral or parenteral administration. Exemplary oral and direct administrations are described or reported in U.S. Pat. No. 4,370,348 (rioprostil ORF-15927); Reele and Bohang *Dig. Dis. Sci*, 29, 390–393 (1984) [$PGE_2$; 15(R),15-methyl $PGE_2$ and 16,16-dimethyl $PGE_2$]; Hunt et al., *Dig. Dis. Sci.*, 28, 897–902 (1983) [misoprostol; SC-29333]; Robert, *Viewpoints on Digestive Disease*, 2, 1–4 (1979) [$PGE_2$; 16,16-dimethyl $PGE_2$; $PGE_{2\beta}$]; Robert et al., *Gastroenterology*, 77, 433–443 (1979) [$PGE_2$; 16,16-dimethyl $PGE_2$; 15(S)-15-methyl $PGF_{2\beta}$; 15(R),15-methyl $PGF_{2\beta}$ and 16,16-dimethyl $PGA_2$]; Johansson and Bergtrom, *Scan. J. Gastroenterol.*, Suppl. Nr. 77, 17, 21–46 (1982) [$PGE_2$; 15(R),15-methyl $PGE_2$; 15(S),15-methyl $PGE_2$; 16,16-dimethyl $PGE_2$; and their methyl esters]; Johansson et al., *Gastroenterology*, 78, 479–483 (1980) [$PGE_2$]; Detweiler et al., Abstract 189, *Gastroenterology*, 86, 1062 (1984) [rioprostil]; Shriver et al., *Arzneim.-Forsch./Drug Research*, 35, 839–843 (1985) [rioprostil]; and Demol et al., *Arzneim. Forsch./Drug Research*, 35, 861–863 (985). The above reports also include intravenous and/or subcutaneous administration (Shriver et al.; Robert et al.; and Johansson and Bergstrom) as well as application directly in the Pavlov pouch of a dog (Johansson and Bergstrom).

U.S. Pat. No. 4,198,521 describes the preparation of 15-deoxy-16-hydroxy-16-vinyl- and cyclopropyl-substituted prostanoic acids and their analogs. That patent broadly teaches that the disclosed compounds are useful as bronchodilators and hypotensive agents, and also for the control of excessive gastric secretion. U.S. Pat. No. 4,254,145 describes the use of the compounds of U.S. Pat. No. 4,198,521 in preparations applied to the skin to lower the systemic blood pressure of treated mammals.

A report by Cervoni et al., *Federation Proc.*, 42, 157–161 (1983) discloses antihypotensive utilities of one compound, ($\pm$)-15-deoxy-16-hydroxy-16 ($\alpha,\beta$) vinyl $PGE_2$ methyl ester (CL 115,347), by oral and topical administration, that was disclosed in both of U.S. Pat. Nos. 4,198,521 and 4,254,145. A report by Birnbaum et al., *Prostaglandins*, 23, 185–199 (1982) provides further disclosures as to the vasodilating use of the same compound as that of the Cervoni et al. article, when that material was applied topically to the skin of laboratory mammals.

BRIEF SUMMARY OF THE INVENTION

The present invention contemplates a method for treating mammalian peptic ulcer disease, and particularly for providing cytoprotection to mammals. In accordance with this invention, mammalian peptic ulcers are treated by topical application of a composition containing an effective amount of a synthetic prostaglandin analog or cogener in a suitable pharmaceutical carrier to the skin of the mammal to be treated. Synthetic prostaglandin analogs which are useful in the present invention have a structure that corresponds to the formula

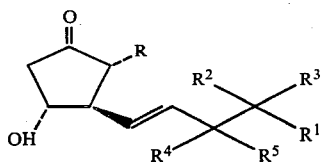

wherein:

R has the formula —$CH_2$—Y—$(CH_2)_2$—Z
wherein —Y— is selected from the group consisting of —$(CH_2)_3$—, cis—HC=CHCH$_2$—, and cis,-cis—HC=C=CH—; and —Z is selected from the group consisting of —CH$_2$OH, and —CO$_2$X, wherein X is hydrogen, a pharmacologically acceptable cation or $C_1$-$C_6$ alkyl;

$R^1$ is n-butyl or phenoxy;

$R^2$ is selected from the group consisting of hydrogen, methyl and hydroxyl;

$R^3$ is selected from the group consisting of hydrogen, methyl and hydroxyl, with the proviso that $R^2$ and $R^3$ cannot both be hydrogen or both be hydroxyl; and $R^4$ and $R^5$ are the same or different and are selected from the group consisting of hydrogen and hydroxyl, but are not both hydroxyl.

A unit dose of the composition is applied topically to the skin of the mammal to be treated, and contact with the skin is maintained for a period of time sufficient for the prostaglandin to penetrate the skin.

Preferred prostaglandin analogs include 16-methyl-1,11α,16RS-trihydroxyprost-13E-en-9-one; methyl(±)-15-deoxy-16RS-hydroxy-16SR-methylprost-13E-en-9-one[(±)9-oxo-11α,16RS-dihydroxy-16SR-methyl-5-cis,13-trans-prostadienoic acid]; (±)9-oxo-11α,15-dihydroxy-16,16-dimethyl-5-cis,13-trans-prostadienoic acid and methyl(±)-9-oxo-11α,15RS-dihydroxy-16,17,18,19-tetranor-20-phenoxy-5-cis, 3-cis,13-trans-prostatrienoate. The composition containing the active ingredient is typically applied from about one to about four times per 24 hour period, or even less frequently, as the case may be, in a suitable pharmaceutical carrier.

The present invention has several benefits and advantages. One benefit is that the invention provides an easy, non-invasive method of treatment as compared to injection or oral administration. The present invention provides the advantage of not delivering a single large dose directly to the stomach or the rest of the gastrointestinal tract and thereby may avoid the nausea, diarrhea and other gastrointestinal distress that often accompanies oral administration of prostaglandins and their analogs or congeners. Several further benefits and advantages will be apparent from the detailed description that follows.

DETAILED DESCRIPTION OF THE INVENTION

Two previously discussed mechanisms are believed to play important roles in the antipeptic ulcer activity of prostaglandins and synthetic prostaglandin analogs and congeners. Those mechanisms include (a) the reduction of the acid burden in the gastrointestinal tract by virtue of gastric acid antisecretory activity, and (b) the cytoprotective increase in the defensive capacity of the gastrointestinal mucosa against many injurious agents.

The present invention contemplates a method for treating mammalian peptic ulcer disease that utilizes prostaglandin analogs that are capable of providing both cytoprotection and gastric acid antisecretory activity at different unit dosages. While others, whose work is discussed before, have reported upon the treatment of peptic ulcer disease using oral, intraduodenal and various injection modes of administration of prostaglandins, their analogs or congeners, the use of the present prostaglandin analogs to treat peptic ulcer disease by topical application has not been previously shown.

As is shown in detail hereinafter, those compounds that can be used to provide treatment for peptic ulcer disease by the oral, intraduodenal or injected administration routes, are not necessarily useful when applied topically to the skin at substantially the same dosage. Thus, utility of a prostaglandin or prostaglandin analog or congener by one means of administration is not predictive or utility by another means of administration for the same or similar compounds.

In accordance with the present invention, a pharmaceutical composition is provided which contains an effective amount of a prostaglandin analog in a pharmaceutical carrier suitable for administration to the skin of a host mammal such as a human or other mammal to be treated.

A useful prostaglandin analog has a structure that corresponds to the formula

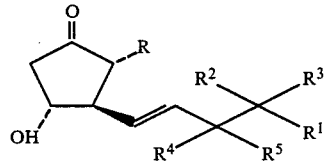

wherein:

R has the formula —$CH_2$—Y—$(CH_2)_2$—Z
wherein —Y— is selected from the group consisting of —$(CH_2)_3$—, cis —HC=CHCH$_2$—, and cis,-cis—HC=C=CH—; and —Z is selected from the group consisting of —CH$_2$OH, and —CO$_2$X, wherein X is hydrogen, a pharmacologically acceptable cation or $C_1$-$C_6$ alkyl;

$R^1$ is n-butyl or phenoxy;

$R^2$ is selected from the group consisting of hydrogen, methyl and hydroxyl;

$R^3$ is selected from the group consisting of hydrogen, methyl and hydroxyl, with the proviso that $R^2$ and $R^3$ cannot both be hydrogen and cannot both be hydroxy; and $R^4$ and $R^5$ are selected from the group consisting of hydrogen and hydroxyl, but are not both hydroxyl.

Pharmacologically acceptable cation salts of carboxylic acids are well known. Useful metal cations include lithium, sodium, potassium, calcium, magnesium, aluminum, zinc and iron.

Pharmacologically acceptable amine cations are those derived from primary, secondary or tertiary amines such as mono-, di- or tri-isopropylamine, N-methylhexylamine, decylamine, dodecylamine, allylamine, crotylamine, cyclopentylamine, cyclohexylamine, allylamine, crotylamine, cyclopentylamine, dicyclohexylamine, mono- or dibenzylamine, alpha- or betaphenylethylamine, ethylenediamine, diethylenetriamine, and arylaliphatic amines containing up to and including 18 carbon atoms such as benzylamine and phenethylamine and the like, as well as heterocyclic amines, e.g., piperidine, morpholine, pyrrolidine, piperazine and lower alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, or triethanolamine, ethyldiethanolamine, N-butylethanolamine, 2-amino-2-methyl-1-propanol, tris(hydroxymethyl)aminomethane, N-phenylethanolamine, N-(p-tert-amylphenyl)diethanolamine, galactamine, N-methylglucamine, N-methylglucosamine, ephredrine, phenylephrine, epinephrine, procaine, and the like.

Examples of suitable pharmacologically acceptable quaternary ammonium cations include tetramethylammonium, tetraethylammonium, benzyltrimethylammonium, phenyltrimethylammonium, and the like.

Thus, compounds such as ammonium, sodium, magnesium, morpholinium, trimethylammonium, and tetramethylammonium($\pm$)9-oxo-11$\alpha$,15-dihydroxy-16,16-dimethyl-5-cis,13-trans-prostadienoate, and 2-methylpiperidinium, diethylammonium, calcium, aluminum, and dodecylammonium($\pm$)9-oxo-11$\alpha$,16RS-dihydroxy-16SR-methyl-13-trans-prostenoate are also useful herein.

Exemplary $C_1$–$C_6$ alkyl (lower alkyl) alcohols from which suitable $C_1$–$C_6$ alkyl portions of carboxylic acid esters (—$CO_2X$ of the formula before) of the useful prostaglandin analogs can be prepared are straight or branched chain aliphatic alcohols that contain 1 to about 6 carbon atoms. Exemplary of such alcohols are methanol, ethanol, propanol, isopropanol, n-butanol, sec-butanol, tert-butanol, 1-pentanol, 2-pentanol 3-pentanol, 2,2-dimethylpropanol, 1-hexanol, 2-hexanol, 3-hexanol, and the like. Thus, compounds such as isopropyl($\pm$)9-oxo-11$\alpha$,15-dihydroxy-16,16-dimethyl-5-cis,13-trans-prostadienoate and 3-hexyl($\pm$)9-oxo-11$\alpha$,16RS-dihydroxy-16SR-methyl-5-cis,13-trans-prostadienoate are also useful herein.

Structural formulae for particular preferred, useful prostaglandin analogs are shown below, along with their chemical and generic names.

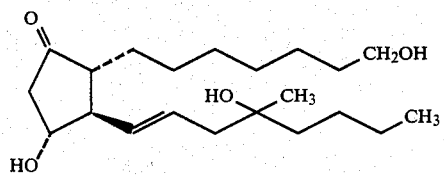

(11$\alpha$,13E)-1,11,16-trihydroxy-16-methyl-prost-13-en-9-one
rioprostil

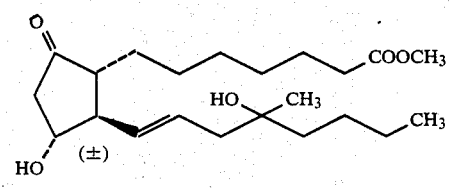

($\pm$)(11$\alpha$,13E)-11,16-dihydroxy-16-methyl-9-oxo-prost-13-en-1-oic acid methyl ester
misoprostol

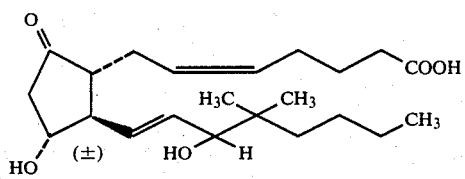

(5Z,11$\alpha$,13E,15R)-11,15-dihydroxy-16,16-dimethyl-9-oxo-prosta-5,13-1-oic acid acid
16,16-dimethyl $PGE_2$

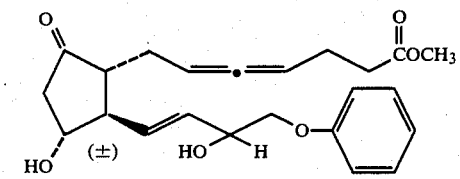

7-[3-hydroxy-2-(3-hydroxy-4-phenoxy-1-butenyl)-5-oxocyclopentyl]-4,5-heptadienoic acid methyl ester
enprostil Of the above materials, rioprostil is particularly preferred as the prostaglandin analog.

The preparation of each of the specific compounds, whose structural formulae are shown above, is described in the literature, as are the preparations of their congeners. Rioprostil is described in U.S. Pat. No. 4,132,738 and its oral use in inducing cytoprotection is described in U.S. Pat. No. 4,370,348. Misoprostol is described in U.S. Pat. Nos. 3,965,143 and 4,459,310, Enprostil is described in U.S. Pat. No. 4,178,457, and 16,16-dimethyl $PGE_2$ is described in U.S. Pat. No. 3,903,139. The disclosures of those patents are hereby incorporated by reference.

As is shown hereinafter, prostaglandins $PGE_1$ and $PGE_2$, and the prostaglandin analog known as trimoprostil, all of whose chemical formuale are shown below, and all of which have structures that are seemingly quite similar to the structures of the prostaglandin analogs of the present invention, were either found to be ineffective at providing cytoprotection when applied topically ($PGE_1$ and $PGE_2$), or were ineffective at significantly inhibiting production of gastric acid, when applied topically (trimoprostil) at the same unit dose at which they were effective by oral or intraduodenal administration. This lack of efficacy points again to the generally unpredictable utility of prostaglandins or prostaglandin analogs or congeners for use in topical treatment of peptic ulcer disease.

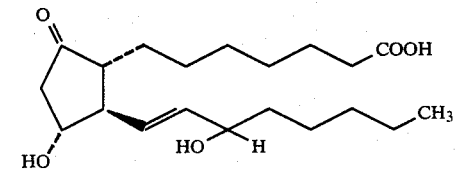

9-oxo-11 alpha,15-dihydroxy-13-trans-prostenoic acid
alprostadil ($PGE_1$)

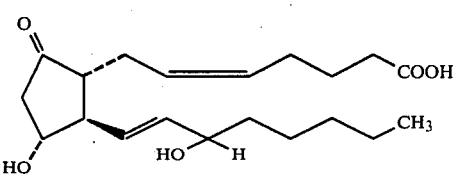

9-oxo-11α,15-dihydroxy-5-cis,13-transprostadienoic acid dinoprostone (PGE₂)

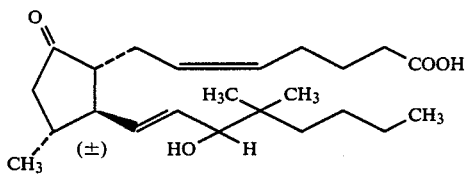

(±)9-oxo-11α-methyl-15-hydroxy-16,16-dimethyl-5-cis,13-trans-prostadienoic acid trimoprostil The pharmaceutical composition contains an effective amount of a prostaglandin analog and is applied to the skin in a unit dose. The amount of the prostaglandin analog in the unit dose varies, inter alia, with the particular active ingredient, the treatment regimen, the host, and the severity of the peptic ulcer disease of the mammal to be treated.

Unit doses for effective cytoprotection are typically much less than doses required for inhibition of gastric acid secretion.

Typically, a unit dose containing from about 0.2 to about 200 micrograms of the prostaglandin per kilogram of body weight is utilized for treating peptic ulcer disease. More preferably, a unit dose contains from about 1 to about 10 micrograms per kilogram of body weight.

The unit dose is generally administered from about one to about four times daily; i.e., per twenty-four time period. More frequent or less frequent applications can also be employed depending upon the means used to administer the compounds. A single administration in which the compound is applied topically once per day using a time release composition is also contemplated, as is discussed hereinafter.

The compound is dissolved or dispersed in a pharmaceutical carrier suitable for topical administration to the skin of the mammal to be treated to form the pharmaceutical composition. Exemplary of hydrophilic pharmaceutical carriers are water miscible organic solvents such as ethanol, propanol, isopropanol, dimethyl sulfoxide (DMSO), propylene glycol, polyethylene glycol having a molecular weight of about 200 to about 1000 that are mixed with a suitable diluent such as water, for example. Petrolatum or other oleaginous material, which is usually used in a water-free, hydrophobic pharmaceutical carrier is also useful.

Various hydrophilic and hydrophobic ointment bases that are mixtures of materials that are well known in the art are also useful as the pharmaceutical carrier. One such ointment carrier is white petrolatum that is employed in combination with antioxidants such as mixed tocopherols to enhance the shelf-life and stability of the formulation. Moreover, the ointment can also employ viscosity modifiers such as paraffin wax, lanolin wax or other compatible solid waxes to adjust the viscosity of the formulation as desired. A typical topical formulation comprises by W/W, from about 75 to 95 percent white petrolatum, 5 to 25 percent of a solubilizer such as diisopropyl adipate or polyethylene glycol (PEG) 2000 dioleate, and about 0.01 to about 2 percent of the prostaglandin analog. As an alternative to employing white petrolatum, a carrier consisting of mineral oil and high molecular weight polyethylene waxes, such as Plastibase®, as supplied by American Cyanamid Company, can be employed.

A pharmaceutically acceptable carrier, whether hydrophilic or hydrophobic, can also include still further ingredients. Exemplary of such further ingredients are sugars, starches, thickeners such as guar gum and carboxymethyl cellulose, and the like as are well known in the art.

Alternatively, the compound can be administered topically through the medium of a drug delivery system. A drug delivery bandage or patch of the type described below, capable of continually administering a metered amount of the treating agent over a prolonged period of time, e.g., 24 hours, can be employed for this purpose. Thus, a continual application of the composition over a 24-hour period can be accomplished by applying a drug delivery bandage or patch to the skin, the bandage or patch containing a 24-hour or longer unit dosage of the composition.

One suitable drug delivery system of the bandage-type comprises a reservoir of the composition disposed between a backing member and a pressure sensitive adhesive layer. The wall of the reservoir adjoining the adhesive layer, and the adhesive layer are permeable to the composition, or at least to the active ingredient and some of the carrier.

In use, the bandage is applied to contact the skin of the treated host mammal so that the adhesive layer forms a tight seal between the skin and the bandage. The active ingredient and at least some of the carrier within the reservoir migrates through the reservoir wall that acts as a solubility membrane, and into the adhesive layer by diffusion. Since the adhesive layer is in contact with the skin, molecules of the active ingredient that are continually removed from the outer surface of the reservoir wall, migrate through the adhesive layer and penetrate (are absorbed by) the skin.

Both the thickness and composition of the reservoir wall-solubility membrane can be adjusted to allow for the metered controlled release of the active ingredient over a prolonged period of time. The reservoir walls can be formed of, for example, the organopolysiloxane rubbers, or the hydrophilic polymers of monoesters of an olefinic acid, such as acrylic and methacrylic acid, as are well known.

The pressure-sensitive adhesive can be formed of any known dermatologically acceptable adhesive that permits migration of the active ingredient, for example: acrylic resins such as polymers of esters of acrylic acid with alcohols such as n-butanol, pentanol, isopentanol, 2-methyl-butanol, 1-methyl-butanol, 1-methyl-pentanol, 2-methyl-pentanol, 3-methyl-pentanol, 2-ethylbutanol, isooctanol, n-decanol, or n-dodecanol, alone or copolymerized with ethylenically unsaturated monomers such as acrylic acid, methacrylic acid, acrylamide, methacrylamide, N-alkoxymethyl acrylamides, N-alkoxymethyl methacrylamides, N-tert-butylacrylamide, itaconic acid, vinylacetate, N-branched alkyl maleamic acids wherein the alkyl group has 10 to 24 carbon atoms, glycol diacrylates, or mixtures thereof; elastomeric silicone polymers; polyurethane elastomers; rubbery polymers, such as polyisobutylene, polyisoprene, polybutadiene; vinyl polymers, such as polyvinylalcohol, polyvinylpyrrolidone, and polyvinylacetate; cellulose derivatives such as ethyl cellulose, methyl cellulose, and carboxymethyl cellulose; natural gums such as guar, acacia, pectins, and the like.

Thus, a sustained release topical dosage of the composition can be contained by the reservoir and administered in metered amounts by the drug-delivery bandage over a prolonged period.

In another embodiment, the drug delivery system can also comprise a backing member carrying a pressure-sensitive adhesive through which permeable microcapsules containing the topically active ingredient is distributed. In use, the bandage is applied to contact the skin as described before, except that the composition migrates from within the microcapsules, which have a function similar to the before-described reservoir. Any of the well-known dermatologically acceptable pressure-sensitive adhesives as are enumerated above and permit migration of the active ingredient can be employed.

Preferred encapsulating materials are the silicon rubbers especially dimethylpolysiloxane, hydrophilic acrylate or methacrylate polymers, polyvinyl acetate, plasticized polyvinyl chloride, plasticized nylon, collagen, gelatin and waxes. The encapsulating material can be uniformly impregnated with the active ingredient or can act as a thin coating around the composition to form microcapsules having interior chambers containing the active ingredient. Alternatively, particles of matrix materials such as starch, gum acacia, gum tragacanth or polyvinylchloride can be impregnated with the solution and encapsulated with one of the other encapsulating materials. The use of matrix and encapsulating membranes of different materials can be employed to slow the rate of release of the prostaglandin. Thus, the matrix or encapsulating membrane plus the active ingredient can comprise the composition.

Examples of suitable bandage-type delivery systems of the type described above are disclosed in whole or in part in U.S. Pat. Nos. 3,598,122, 3,596,123, 4,031,894, 4,060,084, 4,230,687 and 4,359,483, which are incorporated by reference.

The composition containing the active ingredient is maintained in contact with the skin of the host mammal for a period of time sufficient for the prostaglandin to penetrate the skin and be absorbed into the host. As is known in the art, rates of penetration of skin and absorption by a mammal's body vary, inter alia, with the particular prostaglandin being utilized, the amount of compound in contact with the skin, the host mammal, and the pharmaceutically acceptable carrier that is utilized.

As seen in Example 1 below, the prostaglandin penetrates the skin and is generally absorbed into the host mammal's body in less than two hours after application. Cytoprotection was observed about two hours after application of the composition to the skin of the host. Thus, the active ingredient not only penetrated the skin, but was absorbed into the host's body and acted on the stomach mucosa and submucosa within a few hours of its being applied to the skin of the host.

The use of exemplary compounds in the method of this invention to provide cytoprotection and inhibit gastric secretion is described in the Examples below.

EXAMPLE 1

Cytoprotection

Male Charles River rats weighing about 200 g each were fasted overnight, but were allowed water ad libitum. Rats used for the topical administration of this invention were shaved on their dorsal sides one day prior to being used as host mammals.

Compositions containing the active ingredient were prepared for oral administration by dissolving a prostaglandin in a 2 percent aqueous ethanolic solution that was administered in a dose volume of 0.2 milliliters per kilogram (ml/kg) of body weight at the unit dosages shown in Table 1 hereinafter. Compositions for application to the skin were prepared by dissolving the active ingredient in a 25 percent ethanolic water vehicle, and were applied in an amount of 0.2 ml per animal. A fixed concentration for each dose was applied to the skin in a volume of 0.2 ml per rat.

Gastric lesions were induced by oral administration of 1.0 ml of a 50 percent ethanolic water solution that was administered one hour after administration of each of the active ingredients. The rats were sacrificed by asphyxiation one hour after gastric lesion induction using carbon dioxide. The rat stomachs were then removed, inflated with water, opened along the greater curvature, and were laid out on a flat surface. The presence of mucosal bleeding was noted, the mucosal layers were wiped, and the presence or absence of hemorrhagic sites was recorded.

The incidences of lesions compared to controls were statistically analyzed by either the method of Chi-square using Yate's correction or Fisher's Exact Probability Test. Goldstein, *Biostatistics: An Introductory Text*, MacMillan Co., New York, N.Y. (1967).

The results of this study using $PGE_1$, $PGE_2$, rioprostil, misoprostol, 16,16-dimethyl $PGE_2$ ($dmPGE_2$) and enprostil are shown in Table 1, below, as the inhibition of submucosal lesions.

TABLE 1

| | Cytoprotective Activity in Rats | | |
|---|---|---|---|
| | | Percent Inhibition of Submucosal Lesions | |
| Treating Agent | Dose[1] | Oral | Topical |
| $PGE_1$ | 25 | $60^2$ (n = 10)[3] | 10 (n = 10) |
| $PGE_2$ | 25 | $40^2$ (n = 10) | 20 (n = 10) |
| Rioprostil | 25 | $87^2$ (n = 8) | $75^2$ (n = 8) |
| Misoprostol | 100 | $87^2$ (n = 8) | $75^2$ (n = 8) |
| $dmPGE_2$ | 5 | $100^2$ (n = 8) | $100^2$ (n = 8) |
| Enprostil | 5 | $100^2$ (n = 8) | $100^2$ (n = 8) |

[1] Dose in micrograms per kilogram of body weight (μg/kg) for oral administration; for topical administration the dose is expressed as an estimate based on a 200 g rat.
[2] Significant degree of inhibition (p of less than 0.05) compared to pharmaceutically acceptable carrier control.
[3] Parenthesized "n" values are the numbers of animals utilized per condition of administration.

As can be seen from the results obtained above, all of the prostaglandin analogs utilized were effective in inhibiting submucosal lesion when administered orally. However, only rioprostil, misoprostol, 16,16-dimethyl $PGE_2$ and enprostil were effective at the same oral dose when applied externally by contacting the composition with the skin of the host mammal.

EXAMPLE 2

Inhibition of Gastric Acid Secretion

Male Charles River CD rats weighing about 180 g each were shaved on their dorsal sides and derpived of food for a time period of 18 hours prior to use. Water was permitted ad libitim during that time, but was removed during the times at which the rats were studied as host mammals.

The host mammals treated were anesthetized, their abdomens were opened, and the pylorus of each animal was ligated according to the method of Shay et al., *Gastroenterology,* 26, 906–913 (1954). Compositions containing the active ingredient were administered intraduodenally at 1 ml/kg or were applied to directly contact the shaved skin at 0.2 ml/animal at the time the pylorus of each animal was ligated.

The animals were sacrificed by asphyxiation four hours after pylorus ligation using carbon dioxide. The gastric contents were collected in graduated centrifuge tubes that were centrifuged. The centrifugally separated supernatents were then analyzed for volume and acidity. Acid concentration (secretion) was determined by electrometric titration of a 1 ml aliquot of the recovered gastric juice against 0.1N NaOH to a pH value of 7.4.

Treated groups were compared to the control and statistical differences were declared by the method of least significant differences. [Steel, R. G. D. and Torries, J. H., *Principles and Procedures of Statistics,* McGraw-Hill Book Co., N.Y., N.Y., (1960)] as follows:

(treatment-control)/control × 100%

The degree of inhibition of acid secretion (concentration) by rioprostil, misoprostol, trimoprostil, dmPGE$_2$, and enprostil are shown in Table 2, below, for both the intraduodenal and topical administration routes. The compositions employed utilized pharmacologically acceptable carriers of 2 percent ethanolic water and 25 percent ethanolic water for intraduodenal and topical administrations, respectively.

TABLE 2

| Treating Agent | Dose[1] | Effect on Gastric Secretion Percent Inhibition of Acid | |
|---|---|---|---|
| | | Intraduodenal | Topical |
| Rioprostil | 8.0 | 35[2] | 37[2] |
| Misoprostol | 8.0 | 38[2] | 43[2] |
| Trimoprostil | 8.0 | 38[2] | 9 |
| dmPGE$_2$ | 1.0 | 29[2] | 26[2] |
| Enprostil | 1.0 | 71[2] | 32[2] |

[1]Dose in milligrams per kilogram of body weight (mg/kg). (See footnote #1 following Table #1).
[2]Significant degree of inhibition compared to carrier controls. Eight to ten animals were used for each study.

As can be seen from the results obtained above, each of the prostaglandins studied inhibited concentration of gastric acid when administered intraduodenally. However, only applications in accordance with this invention provided a significant inhibition of gastric acid concentration when applied topically at the unit dosage that was effective in the intraduodenal administration.

The foregoing is intended as illustrative of the present invention but not limiting. Numerous variations and modifications can be effected without departing from the true spirit and scope of the novel concepts of the invention.

What is claimed is:

1. A method for topically treating mammalian peptic ulcer disease comprising the steps of:
   (a) providing a composition containing an effective amount of a prostaglandin analog in a pharmaceutical carrier suitable for administration to the skin of the mammal to be treated;
   (b) applying a unit dose of said composition to contact the skin of said mammal to be treated; and
   (c) maintaining said contact for a period of time sufficient for said prostaglandin analog to penetrate the skin; said prostaglandin analog being selected from the group consisting of (11α,13E)-1,11,16-trihydroxy-16-methyl-prost-13-en-9-one; (±)(11α,13E)-11,6-dihydroxy-16-methyl-9-oxo-prost-13-en-1-oic acid methyl ester; (5Z,11α,13E,15R)-11,15-dihydroxy-16,16-dimethyl-9-oxo-prosta-5,13-1-oic acid; and 7-[3-hydroxy-2-(3-hydroxy-4-phenoxy-1-butenyl)-5-oxocyclopentyl]-4,5-heptadienoic acid methyl ester.

2. The method according to claim 1 wherein said unit dose contains about 0.2 to about 200 micrograms per kilogram of body weight of said treated mammal.

3. The method according to claim 1 wherein said composition is applied from about 2 to about 4 times per 24 hour time period.

4. The method according to claim 1 wherein said prostaglandin analog is (11α,13E)-1,11,16-trihydroxy-16-methyl-prost-13-en-9-one.

5. The method according to claim 1 wherein said prostaglandin analog is (±)(11α,13E)-11,16-dihydroxy-16-methyl-9-oxo-prost-13-en-1-oic acid methyl ester.

6. The method according to claim 1 wherein said prostaglandin analog is (5Z,11α,13E,15R)-11,15-dihydroxy-16,16-dimethyl-9-oxo-prosta-5,13-1-oic acid.

7. The method according to claim 1· wherein said prostaglandin analog is 7-[3-hydroxy-2-(3-hydroxy-4-phenoxy-1-butenyl)-5-oxocyclopentyl]-4,5-heptadienoic acid methyl ester.

* * * * *